United States Patent [19]
Kishi et al.

[11] Patent Number: 4,533,546
[45] Date of Patent: Aug. 6, 1985

[54] ANTIINFLAMMATORY ANALGESIC GELLED OINTMENTS

[75] Inventors: Ikuo Kishi, Ichikawa; Hideo Yoshida, Tokyo, both of Japan

[73] Assignee: Lederle (Japan), Ltd., Tokyo, Japan

[21] Appl. No.: 615,531

[22] Filed: May 31, 1984

[30] Foreign Application Priority Data

Jun. 1, 1983 [JP] Japan .................................. 58-95794

[51] Int. Cl.³ ...................... A61K 31/19; A61K 31/78
[52] U.S. Cl. ..................................... 424/81; 514/570; 514/944
[58] Field of Search ........................................... 424/81

[56] References Cited

U.S. PATENT DOCUMENTS

| | | | |
|---|---|---|---|
| 3,749,773 | 7/1973 | Ninger et al. | 424/81 |
| 3,784,704 | 1/1974 | Cohen | 424/317 |
| 4,309,414 | 1/1982 | Inagi et al. | 424/81 |
| 4,393,076 | 7/1983 | Noda et al. | 424/317 |

FOREIGN PATENT DOCUMENTS 886487 4/1981 Belgium .
2482456 11/1981 France .

*Primary Examiner*—Stanley J. Friedman
*Attorney, Agent, or Firm*—Wenderoth, Lind & Ponack

[57] ABSTRACT

An antiinflammatory analgesic gelled ointment comprising a phenylacetic acid type antiinflammatory analgesic agent, a carboxyvinyl polymer in an amount sufficient for gel formation, a water-soluble organic amine, a lower alcohol and water and having a pH in the range of from 7.0 to 9.0.

7 Claims, No Drawings

ANTIINFLAMMATORY ANALGESIC GELLED OINTMENTS

This invention relates to a novel antiinflammatory analgesic gelled ointment, and more specifically, to an antiinflammatory analgesic gelled ointment containing a phenylacetic acid derivative as an anti-inflammatory analgesic agent, which shows a good skin penetrability of the antiinflammatory analgesic agent and less skin irritation.

Many non-steroidal antiinflammatory analgesic agents such as indomethacin, 4-biphenylylacetic acid, ibuprofen and ibufenac have been known. These agents, however, have side-effects on the digestive organs, and cannot be orally administered to patients with peptic ulcer. Hence, for indomethacin, a typical non-steroidal antiinflammatory analgesic agent, a gelled ointment was developed to decrease such side-effects and gained practical acceptance [see, for example, U.K. Patent Application (GB) No. 2,023,000A].

The gelled ointment is an externally applicable drug which has a transparent jelly-like appearance and in which an active agent is substantially completely dissolved in an ointment base. Since the gelled ointment generally has greater skin penetrability of the active agent and is less sticky at the applied site than conventional ointments or creams, much work has been done on it in recent years.

The present inventors made extensive research in order to formulate gelled ointments of phenylacetic acid type antiinflammatory analgesic agents such as 4-biphenylylacetic acid, ibuprofen and ibufenac, particularly 4-biphenylylacetic acid. Since 4-biphenylylacetic acid, ibuprofen, etc. are insoluble or only sparingly soluble in water and various pharmaceutically acceptable solvents, they were unable to give satisfactory gelled ointment forms of good skin penetrability.

It has now been found that the aforesaid phenylacetic acid type antiinflammatory analgesic agents (to be referred to as "active compounds") form uniform gelled ointments with an ointment base composed of a carboxyvinyl polymer as a gelling agent and a mixture of water and a lower alcohol as a solvent, if a water-soluble organic amine is incorporated in the ointment base in an amount much larger than that required to neutralize the carboxyvinyl polymer, and that the resulting ointments permit a very good skin penetrability of the active compounds and are fully acceptable in practical applications.

Thus, according to this invention, there is provided an antiinflammatory analgesic gelled ointment comprising a phenylacetic acid type antiinflammatory analgesic agent (active compound), a carboxyvinyl polymer, a water-soluble organic amine, a lower alcohol and water and having a pH in the range of from 7.0 to 9.0.

The "phenylacetic acid type antiinflammatory analgesic agent" used as an active compound in the present invention denotes an antiinflammatory analgesic compound having a structural moiety of the following formula

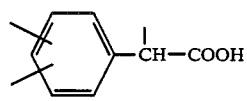

in the molecule, and specifically includes the following compounds.

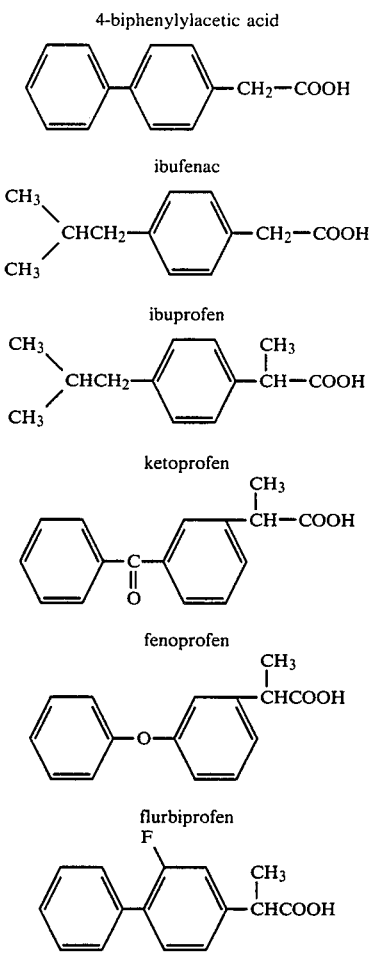

Of these active compounds, 4-biphenylylacetic acid is especially preferred.

The term "lower", as used in the present application, means that a compound or group qualified by this term has not more than 5, preferably not more than 3, carbon atoms.

The carboxyvinyl polymer used as a gelling agent in the ointments of this invention is a cross-linked acrylic acid polymer known also as carboxypolymethylene. It is a water-soluble vinyl polymer containing carboxyl groups in the molecule and having a molecular weight in the range of about 1,000,000 to 3,000,000. For its properties and other details, reference may be made to "Japanese Standards of Cosmetic Ingredients", 1st edition, Supplement, 1971, edited by the Committee on Japanese Standards of Cosmetic Ingredients, The Central Pharmaceutical Affairs Council, the Ministry of Health and Welfare (published by Yakuji Nippon, Ltd.), pages 58–66, and U.S. Pat. No. 2,798,053. Examples of the carboxyvinyl polymer that can be used in this invention are HIVISWAKO-103, 104 and 105 available from Wako Pure Chemicals, Ind. Co., Ltd., Japan, and Carbopol 934, 940 and 941 available from B. F. Goodrich Chemical Co., U.S.A.

As required, the carboxyvinyl polymer may be neutralized with a basic substance to adjust the properties of the resulting gel.

The amount of the carboxyvinyl polymer in the ointment is not strictly fixed, and can be varied over a wide range according to the amounts of the other ingredients, etc. Advantageously, it is 0.5 to 5.0% by weight, preferably 0.5 to 3.0% by weight, more preferably 0.5 to 2.0% by weight, based on the weight of the ointment.

Illustrative of the water-soluble organic amines used in the ointments of the invention are mono(lower alkanol)amines such as monomethanolamine, monoethanolamine, monopropanolamine and monoisopropanolamine; di(lower alkanol)amines such as dimethanolamine, diethanolamine, dipropanolamine, diisopropanolamine, dibutanolamine, diisobutanolamine and di-sec-butanolamine; tri(lower alkanol)amines such as trimethanolamine, triethanolamine, tripropanolamine, triisopropanolamine, tributanolamine, triisobutanolamine and tri-sec-butanolamine; mono(lower alkyl)amines such as methylamine, ethylamine, propylamine and isopropylamine; di(lower alkyl)amines such as dimethylamine, diethylamine, dipropylamine and diisopropylamine; and tri(lower alkyl)amines such as trimethylamine and triethylamine. Of these, the mono-, di- and tri-(lower alkanol)amines are preferred, and diisopropanolamine is especially preferred. These amines may be used singly or in combination.

The characteristic feature of the invention is that the water-soluble organic amine is used in an amount much larger than that required to neutralize the carboxyvinyl polymer. Specifically, it is used in such an amount that the final gelled ointment prepared has a pH in the range of 7.0 to 9.0, preferably 7.0 to 8.0, more preferably 7.3 to 7.8. Conveniently, the amount of the water-soluble amine is 0.5 to 15.0% by weight, preferably 0.5 to 10.0% by weight, more preferably 1.0 to 7.0% by weight, based on the weight of the ointment, although it may vary depending upon the type of the amine, the amounts of the active compound, the carboxyvinyl polymer, etc.

Examples of the lower alcohol used in the ointments of this invention include methanol, ethanol, propanol, isopropanol, butanol, tert-butanol and amyl alcohol. Of these, methanol, ethanol, propanol and isopropanol are preferred. Ethanol is especially preferred.

The lower alcohol may be used in an amount of 5.0 to 50.0% by weight, preferably 10.0 to 40.0% by weight, more preferably 20.0 to 40.0% by weight, based on the weight of the ointment.

The lower alcohol is used as a mixture with water. The ratio of the lower alcohol to water is not strictly fixed, and may be widely varied depending upon the type of the active compound. For example, the weight ratio of the lower alcohol to water is from 1:17 to 5:3, preferably from 1:8 to 1:1, more preferably from 2:7 to 1:1.

Typical proportions of the ingredients in the ointment of this invention are summarized in Table 1.

TABLE 1

| Ingredients | General range (% by weight) | Preferred range (% by weight) | Optimum range (% by weight) |
| --- | --- | --- | --- |
| Active compound | 0.5–8.0 | 0.5–5.0 | 1.0–4.0 |
| Carboxyvinyl polymer | 0.5–5.0 | 0.5–3.0 | 0.5–2.0 |
| Water-soluble organic amine | 0.5–15.0 | 0.5–10.0 | 1.0–7.0 |
| Lower alcohol | 5.0–50.0 | 10.0–40.0 | 20.0–40.0 |
| Water | 30.0–85.0 | 40.0–80.0 | 40.0–70.0 |

TABLE 1-continued

| Ingredients | General range (% by weight) | Preferred range (% by weight) | Optimum range (% by weight) |
| --- | --- | --- | --- |
| Total: | 100 | 100 | 100 |

The gelled ointment of the invention can be prepared from the ingredients described above by mixing them uniformly with stirring in a manner known per se. The ointment of this invention so prepared should be maintained at a pH of 7.0 to 9.0, preferably 7.0 to 8.0, more preferably 7.3 to 7.8, by properly adjusting the amount of the water-soluble organic amine. Desirably, the ointment has a viscosity of 2,000 to 200,000 cps, preferably 10,000 to 100,000 cps.

The gelled ointments provided by this invention have less skin irritation and excellent storage stability, and the active compounds therein exhibit very good skin penetrability and produce great pharmacological effects. Accordingly, they are very useful in practical applications. These advantages of the ointments of the invention are demonstrated by the following experiments conducted by using 4-biphenylylacetic acid as an active compound.

[A] Test on percutaneous absorption

A-1. Animal experiment

A male rat was dehaired at the back, and one day later, the ointment described in Example 2 or an ointment containing the active compound suspended therein as a control was applied in an amount of 1 g/kg to an area of 3×4 cm² in size of the dehaired skin by occlusive dressing technique for 4 hours. Then, the concentration of the active compound in the blood was measured [gas-chromatography-massspectrometer (GC-MS); detecting sensitivity 20 ng/ml]. The results are shown in Table 2. With the ointment of Example 2 in which the active compound was dissolved, the blood level of the active compound was about 4 to 5 times as high as that obtained with the control ointment in which the active compound was suspended. The control ointment contained 2 g of 4-biphenylylacetic acid and 98 g of white Vaseline per 100 g thereof and was prepared by melting white Vaseline on a water bath under heat, uniformly dispersing 4-biphenylylacetic acid in it, and mixing them until the mixture solidified.

TABLE 2

| | Percutaneous absorption test | | |
| --- | --- | --- | --- |
| | Blood level of biphenylyl-acetic acid (ng/ml) | | |
| | after 4 hours | after 8 hours | after 24 hours |
| Suspension (2%) (control) | 1283.0 | 979.0 | 348.0 |
| Ointment of Example 2 (2%) | 6700.0 | 4819.0 | 1306.0 |

A-2. Test on humans (a) Experimental procedure

Six healthy male adult subjects (20 to 26 years old) were divided into two groups each consisting of three subjects (groups A and B). To an area of 900 cm² (30 cm×30 cm) in size of the back of each subject were applied for 8 hours by occlusive dressing technique, 10 g of the gelled ointment obtained in Example 1 (containing 1% of 4-biphenylylacetic acid as an active compound) or the gelled ointment prepared in Example 3 (containing 3% of 4-biphenylylacetic acid as an active compound). The levels of the active compound in the serum before and after the application were measured. The tests were performed by a crossover method as shown below. The second application was effected 10 days after the first application.

| Subjects | First application | Second application |
|---|---|---|
| Group A (three subjects) | Gelled ointment of Example 1 | Gelled ointment of Example 3 |
| Group B (three subjects) | Gelled ointment of Example 3 | Gelled ointment of Example 1 |

Blood was drawn from the vein of the upper arm of each subject seven times in total, i.e. at 2, 4, 8, 12, 24 and 48 hours. The blood was centrifuged, and the levels of the active compound in the serum obtained were measured by GC-MS (GC: HITACHI Model 367, MS: HITACHI Model M-80; detection limit: 10 ng/ml).

(b) Experimental results

The results are shown in Table 3. The concentration of 4-biphenylylacetic acid in the serum after single application of the gelled ointment of Examples 1 and 3 reached a peak 24 hours after the application, and the drug was absorbed through the skin in a high concentration.

TABLE 3

Level of 4-biphenylylacetic acid in serum (average values obtained from six subjects)

| | Before application | Level of drug in serum after application of gelled ointment (ng/ml) | | | | | |
|---|---|---|---|---|---|---|---|
| | | 2 hours | 4 hours | 8 hours | 12 hours | 24 hours | 48 hours |
| Gelled ointment of Example 1 (± S.E.) | 0 | 23 (±5) | 43 (±7) | 89 (±22) | 139 (±31) | 190 (±18) | 46 (±17) |
| Gelled ointment of Example 3 (± S.E.) | 0 | 35 (±6) | 55 (±11) | 120 (±27) | 201 (±46) | 411 (±31) | 90 (±19) |

[B] Pharmacological test

B-1. Inhibitory activity on carrageenin-induced paw edema in rats (a) Experimental animals Ten-member groups of CRJ-CD(SD)-strain male rats (6 to 7 weeks old) were used.

(b) Test drugs

Gelled ointments (prepared in Examples 1, 2 and 3) containing 1, 2 and 3% by weight, respectively, of 4-biphenylylacetic acid.

(c) Experimental procedure

The volume of the left hind paw of each rat was measured, and then 1% carrageenin solution as an inflammation inducing agent was injected subcutaneously at the paw in an amount of 0.1 ml per rat. From three hours before the injection of the inflammation inducing agent to the time of injection, each of the test drugs was applied to the entire left hind paw three times in an amount of 100 mg each time (total 300 mg). After the injection, the volume of the paw was measured every one hour up to 5 hours after the injection. The percent of edema and the percent of inhibition of edema were calculated in accordance with the following equations.

$$\text{Percent of edema (\%)} = \frac{V_1 - V_o}{V_o} \times 100$$

$V_o$: the volume of the paw before injection of the inflammation inducing agent $V_1$: the volume of the paw after injection of the inflammation inducing agent at each indicated time.

$$\text{Percent of inhibition of edema (\%)} = \frac{E_c - E_t}{E_c} \times 100$$

$E_c$: the percent edema (average) of the intact control group at each indicated time, $E_t$: The percent edema (average) of each medicated group at each indicated time.

(d) Results

The results are shown in Table 4. The results suggest that the gelled ointments containing 4-biphenylylacetic acid so applied produced an edema inhibitory effect starting at 1 hour after the injection of the inflammation inducing agent. This effect was dose-dependent, and the gelled ointment containing 3% by weight of 4-biphenylylacetic acid showed a significant edema-inhibitory effect which lasted up to 5 hours after the injection of the inflammation inducing agent.

TABLE 4

| Concentration of 4-biphenylylacetic acid (%) | Percent of edema (%) (Edema-inhibitory percent, %) | | | | |
|---|---|---|---|---|---|
| | After 1 hour | After 2 hours | After 3 hours | After 4 hours | After 5 hours |
| Control | 18.9 | 58.1 | 67.8 | 62.6 | 62.4 |
| 1 (Example 1) | 11.5* (39.2) | 39.4** (32.2) | 58.2 (14.2) | 54.8 (12.5) | 56.8 (9.0) |
| 2 (Example 2) | 10.7 (43.4) | 35.6** (38.7) | 46.7** (31.1) | 47.7** (23.8) | 50.8 (18.6) |
| 3 (Example 3) | 9.3** (50.8) | 32.4** (44.2) | 44.5** (34.4) | 47.7** (23.8) | 49.9* (20.0) |

*P<0.05,
**P<0.01

B-2. Inhibitory activity on adjuvant-induced arthritis (a) Experimental animals

Fifteen-member groups of CRJ-CD (SD)-strain female rats (6 to 7 weeks old) were used.

(b) Test drugs

Gelled ointments prepared in Examples 1, 2 and 3 containing 1, 2 and 3%, respectively, of 4-biphenylylacetic acid.

(c) Experimental procedure

As an adjuvant, 0.6 mg of heat-killed cells of *Mycobacterium butyricum* suspended in liquid paraffin was injected subcutaneously into the left hind paw of each rat. Each of the test drugs was applied to the entire left hind paw twice a day at a three-hour interval in an amount of 100 mg each time (a total of 200 mg in six hours) over a period of 14 days after the injection of the adjuvant. After the lapse of six hours, the drug remaining on the left hind paw was wiped off. The symptom of arthritis was determined by measuring the volumes of both hind paws periodically up to the 21st day after the injection of the adjuvant, and calculating the percent edema in accordance with the following equation.

$$\text{Percent of edema (\%)} = \frac{V_1 - V_o}{V_o} \times 100$$

$V_o$: the volume of the paw before the injection of the adjuvant $V_1$: the volume of the paw at each indicated day after the injection of the adjuvant (d) Experimental results The results are shown in Tables 5 and 6. The results showed that the edema at the left hind paw into which the adjuvant was injected was markedly inhibited from the early stage by the application of the gelled ointments containing 4-biphenylylacetic acid in various concentrations, and this inhibitory activity was dose-dependent. Furthermore, a significant edema inhibitory action lasted until the 21st day after the injection of the adjuvant, which corresponded to the 7th day after the completion of application of the drug. At the right hind paw into which the adjuvant was not injected, edema was observed on the 11th day, but on the 13th day onward, the inhibitory activity of the drug appeared, and lasted until the 21st day.

TABLE 5

| Concentration of 4-biphenylyl-acetic acid (% by weight) | Percent of edema (%) (Edema-inhibitory percent, %) | | | | |
| --- | --- | --- | --- | --- | --- |
| | 1st day | 7th day | 11th day | 12th day | 21st day |
| Control | 74.0 | 117.8 | 170.3 | 183.4 | 225.3 |
| 1 | 69.2 | 80.4** | 102.3** | 104.6 | 175.6* |
| (Example 1) | (6.5) | (31.8) | (39.9) | (43.0) | (22.1) |
| 2 | 69.1 | 74.5** | 87.6** | 91.4 | 167.5* |
| (Example 2) | (6.6) | (36.8) | (48.6) | (50.2) | (25.7) |
| 3 | 61.8** | 59.7** | 68.8** | 74.0 | 157.5** |
| (Example 3) | (16.5) | (49.3) | (59.6) | (59.7) | (30.1) |

*$P<0.05$,
**$P<0.01$

TABLE 6

| Concentration of 4-biphenylyl-acetic acid (%) | Percent of edema (%) (Edema-inhibitory percent, %) | | | | |
| --- | --- | --- | --- | --- | --- |
| | 1st day | 7th day | 11th day | 13th day | 21st day |
| Control | −7.9 | −4.8 | 5.8 | 24.9 | 69.0 |
| 1 | −4.0 | −2.5 | 0.7 | 7.9* | 41.5* |
| (Example 1) | (49.4) | (47.9) | (87.9) | (68.3) | (39.9) |
| 2 | −5.2 | −2.1 | −1.3 | 8.0* | 61.3 |
| (Example 2) | (34.2) | (56.3) | (122.4) | (67.9) | (11.2) |
| 3 | −1.1 | −1.9 | −2.1 | 2.7** | 30.2** |
| (Example 3) | (86.1) | (60.4) | (136.2) | (89.2) | (56.2) |

*$P<0.05$,
**$P<0.01$

B-3: Inhibitory activity on formation of granuloma (cotton pellet method)

(a) Experimental animals

Ten-member groups of CRJ-CD (SD) male rats (6 to 7 weeks old) were used.

(b) Test Drug

A gelled ointment containing 3% of 4-biphenylylacetic acid (prepared in Example 3) was used.

(c) Experimental procedure

Under anesthesia, the skin of each rat was incised mesially at the back, and 30 mg of sterilized cotton pellets were implanted beneath the skin on both sides of the mesial line. The test drug was applied to the skin (about 10 cm$^2$) where the cotton pellets were implanted twice a day in an amount of 100 mg each time over seven days including the day of operation. On the 8th day, the cotton pellets were taken out, and the dry weight of granuloma growing around the cotton pellets was measured.

(d) Experimental results

The results are shown in Table 7. The application of the gelled ointment containing 3% of 4-biphenylylacetic acid significantly inhibited the formation of granuloma. The percent of inhibition was 18.9%.

TABLE 7

| Test drugs | Granuloma | |
| --- | --- | --- |
| | Weight (mg) | Percent of inhibition (%) |
| Control | 71.0 | — |
| Gelled ointment containing 3% of 4-biphenylylacetic acid (Example 3) | 57.6** | 18.9 |

**$P<0.01$.

B-4. Inhibitory activity on edema at the ear induced by croton oil (a) Experimental animals Fourteen-member groups of CRJ-CD (SD)-strain rats (3 to 4 weeks old) were used.

(b) Test drug

A gelled ointment containing 3% of 4-biphenylylacetic acid (Example 3).

(c) Experimental procedure

1% Croton oil was applied to the right ear of each rat, and 5 minutes later and 3 hours later, 100 mg of the test drug was applied to the right ear. Six hours after the application of the drug, both ears were cut off under anesthesia, and their weights were measured. The percent of edema was calculated in accordance with the following equation.

$$\text{Percent of edema (\%)} = \frac{W_t - W_c}{W_c} \times 100$$

$W_c$: the weight of the left ear to which the edema-inducing agent was not applied, $W_t$: the weight of the right ear to which the edema-inducing agent was applied.

(d) Experimental results

The results are shown in Table 8. The application of the gelled ointment containing 3% of 4-biphenylylacetic acid markedly inhibited the formation of edema of the ear induced by croton oil, and the percent of inhibition was 72.7%.

TABLE 8

| Test drugs | Edema of the ear | |
| --- | --- | --- |
| | Percent of edema (%) | Percent of inhibition (%) |
| Control | 57.2 | — |
| Gelled ointment containing 3% of 4-biphenylylacetic acid (Example 3) | 15.6** | 72.7 |

**$P<0.01$

B-5. Analgesic activity (the Randull-Selitto method)

(a) Experimental animals

Ten-member groups of CRJ-CD (SD) male rats (6 to 7 weeks old) were used.

(b) Test drug

A gelled ointment containing 3% by weight of 4-biphenylylacetic acid, prepared in Example 3 was used.

(c) Experimental procedure

To both hind paws of each rat was applied 200 mg of the test drug three times at 1-hour intervals. A 20% suspension of beer yeast (0.1 ml) as an inflammation inducing agent was subcutaneously administered to the left hind paw. The pressure pain threshold value was measured 2, 3 and 4 hours after the administration of the inflammation inducing agent.

(d) Experimental results

The results are shown in Table 9. The test drug showed a significant analgesic action.

TABLE 9

| | | | Analgesic activity-yeast-inflamed rat paw-pressure threshold method | | | |
|---|---|---|---|---|---|---|
| | | Concentration | Pressure Pain Threshold (Ratio) Mean ± S.D. | | | |
| Compound | Dose (mg/paw) | of Drug in Vehicle (%) | Before application | After 2 hr | After 3 hr | After 4 hr |
| Untreated control | — | — | 8.15 ± 1.44 (1.000) | 5.08 ± 1.29 (0.623) | 4.93 ± 1.19 (0.605) | 4.88 ± 1.57 (0.599) |
| Vehicle control | 200 | 0 | 7.93 ± 1.02 (1.000) | 4.73 ± 0.69 (0.596) | 4.43 ± 0.47 (0.559) | 5.20 ± 1.23 (0.656) |
| Ointment of Example 3 | 200 | 3 | 7.98 ± 1.47 (1.000) | 6.43 ± 2.05 (0.806) | 6.40 ± 1.47* (0.802) | 7.25 ± 1.50** (0.909) |

*$P < 0.05$,
**$P < 0.01$

[C] Skin irritation test (a) Experimental animals

Six male rabbits (Japanese native white strain) were used.

Intact skin group: Dehaired by a hair clipper
Abraded skin group: dehaired by a hair clipper followed by removing horny layer.

(b) Experimental procedure

A 1 cm² gauze coated with the gelled ointment of Example 3 (containing 3% by weight of 4-biphenylylacetic acid) or the gel ointment base was applied to a test site of the rabbits for 24 hours. The applied part was covered with a vinyl polymer film, sealed with a tape and then protected by a supporter. The skin irritation of the drug was evaluated by the Draize method using erythema, incrustation and edema as indices immediately after wiping off the gelled ointment, and 24 hours, and 48 hours later.

(c) Experimental results

The results are shown in Table 10. The gelled ointment of Example 3 did not show any skin irritation to the rabbits both in the skin intact group and the skin abraded group.

TABLE 10

| | | Skin irritation in rabbits - skin irritation total scores (Draize test) | | | | | | |
|---|---|---|---|---|---|---|---|---|
| | | Irritation Score after Administration | | | | | | |
| | Study | Abraded Skin | | | Intact Skin | | | |
| Formulations | Animal Number | 24 hr | 48 hr | 72 hr | 24 hr | 48 hr | 72 hr | Combined Average |
| Untreated | 0001 | 0 | 0 | 0 | 0 | 0 | 0 | 0 |
| | 0002 | 0 | 0 | 0 | 0 | 0 | 0 | |
| Gel Base | 0003 | 0 | 0 | 0 | 0 | 0 | 0 | 0 |
| | 0004 | 0 | 0 | 0 | 0 | 0 | 0 | |
| The ointment of Example 3 | 0005 | 0 | 0 | 0 | 0 | 0 | 0 | 0 |
| | 0006 | 0 | 0 | 0 | 0 | 0 | 0 | |

[D] Test on the stability of the gelled ointments

The gelled ointments prepared in Examples 1 to 3 were subjected to a stability test for 6 months, and the results are shown in Table 11. When stored at 40° C. for 6 months, no change was observed in the appearance of the ointments, nor was there a decrease in potency or a change in pH and viscosity.

TABLE 11

| | | Stability test (40° C.) | | | |
|---|---|---|---|---|---|
| | | | Periods | | |
| | | Immediately after production | 1 month | 3 months | 6 months |
| Example 1 | Measured value (mg/g) (residual ratio, %) | 10.1 (100.0) | 10.2 (101.0) | 10.0 (99.0) | 10.0 (99.0) |
| | Appearance | Colorless transparent gel | — | — | — |
| | pH | 7.4 | 7.4 | 7.4 | 7.4 |
| | Viscosity (cps) | 56000 | 58000 | 55000 | 56000 |
| Example 2 | Measured value (mg/g) (residual ratio, %) | 20.0 (100.0) | 20.0 (100.0) | 19.9 (99.5) | 20.0 (100.0) |
| | Appearance | Colorless transparent gel | — | — | — |
| | pH | 7.5 | 7.5 | 7.5 | 7.5 |
| | Viscosity (cps) | 35000 | 35000 | 35000 | 35000 |
| Example 3 | Measured value (mg/g) (residual ratio, %) | 30.2 (100.0) | 30.1 (99.7) | 30.1 (99.7) | 30.1 (99.7) |
| | Appearance | Colorless transparent gel | — | — | — |
| | pH | 7.6 | 7.6 | 7.6 | 7.6 |
| | Viscosity (cps) | 28000 | 27000 | 27000 | 28000 |

—: No change

The following Examples illustrate the present invention in greater detail.

All viscosities in these examples were measured at 20° C. by means of a E-type viscometer supplied by Tokyo Keiki K.K.

EXAMPLE 1

| | |
|---|---|
| HIVISWAKO 104 (a product of Wako Pure Chemicals, Ind. Co., Ltd.) | 1.0 g |
| 4-Biphenylylacetic acid | 1.0 |
| Diisopropanolamine | 2.0 |
| Ethanol | 35.0 |
| Pure water to make | 100 |

HIVISWAKO 104 was swollen in a mixture of 20 g of pure water and ethanol. Separately, diisopropanolamine and 4-biphenylylacetic acid were dissolved in 10 g of pure water. The two solutions were mixed, and the remainder of pure water was added. The mixture was stirred until it became uniform (pH 7.4, viscosity 56000 cps).

EXAMPLE 2

| HIVISWAKO 104 | 1.0 g |
|---|---|
| 4-Biphenylylacetic acid | 2.0 |
| Diisopropanolamine | 2.7 |
| Ethanol | 35.0 |
| Pure water to make | 100 |

HIVISWAKO 104 was swollen in a mixture of 20 g of pure awater and ethanol. Separately, diisopropanolamine and 4-biphenylylacetic acid were dissolved in 10 g of pure water. The two solutions were mixed, and the remainder of pure water was added. The mixture was stirred until it became uniform (pH 7.5, viscosity 35000 cps).

EXAMPLE 3

| HIVISWAKO 104 | 1.0 g |
|---|---|
| 4-Biphenylylacetic acid | 3.0 |
| Diisopropanolamine | 3.5 |
| Ethanol | 35.0 |
| Pure water to make | 100 |

HIVISWAKO 104 was swollen in a mixture of 20 g of pure water and ethanol. Separately, diisopropanolamine and 4-biphenylylacetic acid were dissolved in 10 g of pure water. The two solutions were mixed, and the remainder of pure water was added. The mixture was stirred until it became uniform (pH 7.6, viscosity 28000 cps).

EXAMPLE 4

| HIVISWAKO 104 | 1.0 g |
|---|---|
| Ibuprofen | 3.0 |
| Triethanolamine | 3.5 |
| Isopropanol | 25.0 |
| Pure water to make | 100 |

HIVISWAKO 104 was swollen in a mixture of 20 g of pure water and isopropanol. Separately, triethanolamine and ibuprofen were dissolved in 10 g of pure water. The two solutions were mixed, and the remainder of the pure water was added. The mixture was stirred until it became uniform (pH 7.4, viscosity 25000 cps).

EXAMPLE 5

| HIVISWAKO 104 | 2.0 g |
|---|---|
| 4-Biphenylylacetic acid | 4.0 |
| Triisopropanolamine | 6.2 |
| Isopropanol | 30.0 |
| Pure water to make | 100 |

HIVISWAKO 104 was swollen in a mixture of 20 g of pure water and isopropanol. Separately, triisopropanolamine and 4-biphenylylacetic acid were dissolved in 10 g of pure water. The mixture was stirred until it became uniform (pH 7.4, viscosity 72000 cps).

EXAMPLE 6

| HIVISWAKO 104 | 2.0 g |
|---|---|
| Ibufenac | 4.0 |
| Triisopropanolamine | 6.8 |
| Ethanol | 25.0 |
| Pure water to make | 100 |

HIVISWAKO 104 was swollen in a mixture of 20 g of pure water and ethanol. Separately, triisopropanolamine and ibufenac were dissolved in 10 g of pure water. The two solutions were mixed, and the remainder of pure water was added. The mixture was stirred until it became uniform (pH 7.8, viscosity 77000 cps).

EXAMPLE 7

| HIVISWAKO 104 | 1.0 g |
|---|---|
| Ketoprofen | 2.0 |
| Diisopropanolamine | 2.6 |
| Ethanol | 35.0 |
| Pure water to make | 100 |

HIVISWAKO 104 was swollen in a mixture of 20 g of pure water and ethanol. Separately, diisopropanolamine and ketoprofen were dissolved in 10 g of pure water. The two solutions were mixed, and the remainder of pure water was added. The mixture was stirred until it became uniform (pH 7.6, viscosity 36000 cps).

What is claimed is:

1. An antiinflammatory analgesic gelled ointment consisting essentially of
   (a) 0.5 to 8% by weight of 4-biphenylylacetic acid,
   (b) 0.5 to 5% by weight of a carboxyvinyl polymer, having a molecular weight in the range of 1,000,000 to 3,000,000,
   (c) 0.5 to 15% by weight of a water-soluble organic amine selected from mono-, di- and tri-lower alkanol amines,
   (d) 5 to 50% by weight of a lower alkanol selected from the group consisting of methanol, ethanol, propanol, isopropanol, butanol, tert-butanol and amyl alcohol, and
   (e) water in an amount sufficient to make up the balance of the ointment, the amount of the organic amine being such that the ointment has a pH in the range of from 7.0 to 9.0.

2. A gelled ointment according to claim 1 which has a pH in the range of from 7.0 to 8.0.

3. A gelled ointment according to claim 1 wherein the water-soluble organic amine is diisopropanolamine.

4. A gelled ointment according to claim 1 wherein the lower alcohol is methanol, ethanol, propanol or isopropanol.

5. A gelled ointment according to claim 4 wherein the lower alcohol is ethanol.

6. A gelled ointment according to claim 1 which contains 5.0 to 50.0% by weight of the lower alcohol and 30.0 to 85.0% by weight of water based on the weight of the ointment.

7. A gelled ointment according to claim 1 comprising 0.5 to 8.0% by weight of 4-biphenylylacetic acid, 0.5 to 3.0 by weight of the carboxyvinyl polymer, 0.5 to 10.0% by weight of the water-soluble organic amine, 10.0 to 40.0% by weight of the lower alcohol and 40.0 to 80.0% by weight of water, all based on the weight of the ointment, and having a pH in the range of from 7.0 to 8.0.

* * * * *